United States Patent [19]
Funk et al.

[11] Patent Number: 5,523,503
[45] Date of Patent: Jun. 4, 1996

[54] COCURRENT SIMULATED MOVING BED HYDROCARBON ALKYLATION PROCESS

[75] Inventors: Gregory A. Funk, Carol Stream; Simon H. Hobbs, Chicago; Anil R. Oroskar, Downers Grove; Stanley A. Gembicki, Clarendon Hills; Joseph A. Kocal, Gurnee, all of Ill.

[73] Assignee: UOP, Des Plaines, Ill.

[21] Appl. No.: 274,512

[22] Filed: Jul. 13, 1994

[51] Int. Cl.$^6$ ................................. C07C 2/64; C07C 2/56
[52] U.S. Cl. ..................... 585/446; 585/323; 585/331; 585/709; 585/714; 585/716
[58] Field of Search ..................... 585/323, 446, 585/449, 467, 709, 714, 716, 331

[56] References Cited

U.S. PATENT DOCUMENTS

| | | | |
|---|---|---|---|
| 3,851,004 | 11/1974 | Yang | 260/671 C |
| 4,008,291 | 2/1977 | Zabransky et al. | 260/683.43 |
| 4,028,430 | 6/1977 | Stine et al. | 260/683.43 |
| 4,139,573 | 2/1979 | Carson | 260/683.49 |
| 4,973,780 | 11/1990 | Johnson et al. | 585/467 |
| 5,004,853 | 4/1991 | Barger et al. | 585/481 |
| 5,146,037 | 9/1992 | Zarchy et al. | 585/738 |
| 5,284,992 | 2/1994 | Hotier et al. | 585/805 |

*Primary Examiner*—Ponnathapura Achutamurthy
*Attorney, Agent, or Firm*—Thomas K. McBride; John F. Spears, Jr.

[57] ABSTRACT

Hydrocarbons such as isobutane and benzenes are alkylated using a solid catalyst in a process which simulates the cocurrent movement of the catalyst bed versus the reactants. This has been found to greatly reduce the rate of catalyst deactivation compared to simulated countercurrent flow. The process may be performed using five or more beds of catalyst, with two undergoing regeneration at any one time. One bed is subjected to a short term liquid-phase regeneration while the other is subjected to long term vapor-phase regeneration. The catalyst preferably contains a metal hydrogenation function effective to selectively hydrogenate $C_6$-plus materials trapped on the used catalyst.

15 Claims, 3 Drawing Sheets

COUNTERCURRENT

COCURRENT

COCURRENT SIMULATED MOVING BED HYDROCARBON ALKYLATION PROCESS

BACKGROUND OF THE INVENTION

1. Field of the Invention

The invention relates to a hydrocarbon conversion process. The invention specifically relates to the alkylation of hydrocarbons such as aromatics or paraffins to produce useful chemicals and motor fuel. The invention is primarily directed to a process for the solid bed alkylation of isobutane to produce $C_8$ isoparaffins useful as motor fuel blending components.

2. Related Art

Large amounts of high octane gasoline are produced by the alkylation of isobutane with butenes. Likewise, large amounts of valuable aromatic hydrocarbons including cumene, ethylbenzene and $C_{10}$–$C_{15}$ linear alkylaromatics are produced by the alkylation of benzene with olefins of the appropriate carbon number. The variety of feed reactants and the passage of time has led to the development of a number of effective alkylation technologies which are employed in large scale commercial facilities.

One of the most widely used processes for the production of motor fuel is HF alkylation as described in U.S. Pat. No. 4,139,573 issued to D. B. Carson, which provides an overview of the HF alkylation process. One of the advantages of the use of liquid-phase HF as a catalyst is its resistance to deactivation, and the relative ease with which a slipstream may be removed from an onstream reaction zone for "regeneration". The HF itself is not chemically changed during use but various organic reaction by-products such as "acid soluble oils" (ASO) accumulate in the liquid-phase HF and are removed during this regeneration.

Regeneration is also necessary for all solid bed motor fuel alkylation catalysts developed to date since they tend to suffer from a high deactivation rate. Deactivation of solid catalysts is due to different, possibly multiple, causes from those encountered with liquid HF as a catalyst and usually includes some accumulation of hydrocarbonaceous deposits on the catalyst.

A common method of regenerating catalysts is by combustion of organic deposits. This is often not desired for alkylation catalysts. U.S. Pat. No. 3,851,004 to C. L. Yang describes an alternative method for regenerating a solid bed alkylation catalyst comprising a hydrogenation component on a zeolitic support which comprises contacting the catalyst with a hydrogen-containing liquid-phase saturated hydrocarbon.

Any interruption in the operation of the reaction zone to regenerate or replace catalyst is undesirable. Certain operating benefits are provided to any process by an ability to operate in a continuous manner, which makes it desirable to find a means to regenerate or replace the catalyst while the reaction zone is kept in use. U.S. Pat. No. 4,973,780 issued to R. C. Johnson et al describes a moving bed alkylation process in which catalyst is continuously or periodically replaced with regenerated catalyst to provide countercurrent catalyst reactant flows.

It has also been proposed to provide continuous operation by simulating the movement of the catalyst through the reaction and regeneration zones. U.S. Pat. Nos. 4,008,291 to R. F. Zabransky et al. and 4,028,430 to L. O. Stine et al. describe the use of simulated countercurrent operations to perform a number of alkylation reactions including the production of motor fuel. These references provide separate reaction and catalyst reactivation zones, with an external regenerant stream being employed for the reactivation. In both references the effluent of the reaction zone is withdrawn from the alkylation zone immediately upon its exit from the reaction zone. These references also teach the use of a "pump around" stream to complete the simulation and provide a continuous liquid loop. U.S. Pat. No. 4,008,291 discloses in column 17 that a portion of the reaction zone effluent may be recycled to the reaction zone to increase the paraffin to olefin ratio in the reaction zone.

BRIEF SUMMARY OF THE INVENTION

The invention is a simulated cocurrent moving bed solid catalyst alkylation process. The invention increases catalyst life, which is the primary problem facing the commercialization of solid bed alkylation for the production of motor fuels. The invention is characterized by the simulation of cocurrent movement of the catalyst and process fluids in the alkylation zone. A limited embodiment of the invention relates to a unique method of regeneration in which two different beds are subjected to different modes of regeneration.

One broad embodiment of the invention may be characterized as a simulated cocurrent moving bed process for the alkylation of a feed hydrocarbon performed in an apparatus preferably comprising at least five individual beds of catalyst divided between a multibed alkylation zone and a regeneration zone, which process comprises the steps passing a first feed stream, which comprises a feed hydrocarbon, and an alkylating agent into a first catalyst bed of the multibed reaction zone with the first catalyst bed containing a fixed bed of a solid alkylation catalyst and operated at alkylation-promoting conditions, reacting the feed hydrocarbon and at least a portion of the alkylating agent to produce a product hydrocarbon while the feed stream passes through the reaction zone and thereby forming a first catalyst bed effluent stream comprising the feed hydrocarbon and the product hydrocarbon; passing the first catalyst bed effluent stream into a second catalyst bed of the reaction zone, comprising a fixed bed of the solid alkylation catalyst and operated at alkylation promoting conditions, reacting the feed hydrocarbon and the alklating agent to produce an additional quantity of the product hydrocarbon and thereby forming a second catalyst bed effluent stream comprising the feed hydrocarbon and the product hydrocarbon; recovering the product hydrocarbon from the second catalyst bed effluent stream; passing a liquid-phase regenerant stream through the regeneration zone, which comprises a third catalyst bed comprising a fixed bed of the solid alkylation catalyst and operated at regeneration conditions; and, periodically advancing the locations at which the first feed stream and the regenerant stream enter the process, the second catalyst bed effluent stream is removed from the process and the identity of the catalyst bed undergoing regeneration to simulate the cocurrent movement of the beds of catalyst relative to the direction of flow of the first and second feed streams through the reaction zone.

As used herein the term "substantially free" means a molar concentration less than 1.5 mole percent. The term "rich" is intended to indicate a concentration of the specified compound or class of compounds greater than 50 mole percent.

DETAILED DESCRIPTION AND PREFERRED EMBODIMENTS

Figure 1:
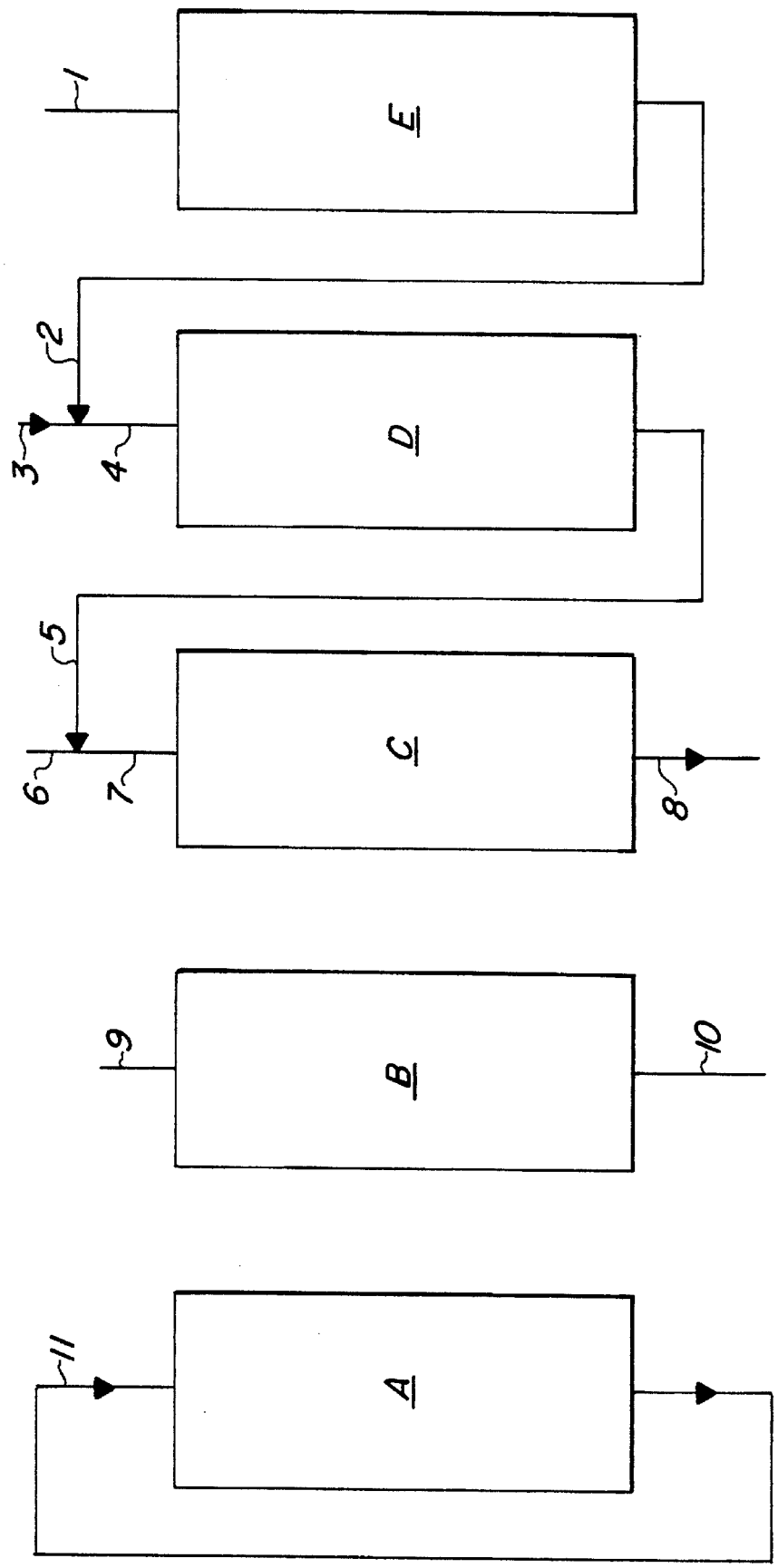
FIG. 1 is a simplified flow diagram of a process unit for the production of motor fuel in a cocurrent simulated moving bed alkylation zone having five separate catalyst beds labeled A–E.

Hydrocarbon alkylation is widely used in the petroleum refining and petrochemical industries to produce a variety of useful acyclic and cyclic hydrocarbon products used in motor fuel, plastics, detergents and petrochemicals. Much of the installed base of alkylation capacity uses liquid phase hydrofluoric acid, generally referred to as HF, as the catalyst to produce $C_8$ gasoline blending components and alkyl aromatics. The petroleum industry continues to use HF acid as the alkylation catalyst of choice due to the high octane fuel it produces together with other operational advantages. The use of HF in these applications has a long record of highly dependable and safe operation. However, the potential damage from an unintentional release of any sizeable quantity of HF and the need to safely dispose of some by-products formed in product or effluent treating procedures has led to an increasing demand for alkylation process technology which does not employ HF as the catalyst.

It is an objective of this invention to provide an alkylation process which does not employ liquid phase HF as the catalyst. It is a further objective of the subject process to provide an improved simulated moving bed alkylation process. It is a specific objective of the invention to provide a solid bed motor fuel alkylation process for the production of $C_8$ branched chain hydrocarbons.

The subject invention achieves these objectives by the use of a unique flow scheme that simulates cocurrent flow of the reactants and the catalyst in the reaction zone.

The preferred feed hydrocarbon to the subject process is isobutane, which is reacted with a $C_3$ to $C_5$ olefin, preferably a butene, to produce "alkylate" for use as gasoline boiling range motor fuel. The feed hydrocarbon or hydrocarbon substrate may vary to include other hydrocarbons including $C_3$ and $C_5$ paraffins. Another preferred feed hydrocarbon is benzene, which may be alkylated with a wide range of feed olefins including ethylene, propylene and butylene to produce such chemicals as ethylbenzene and cumene. A large amount of benzene is alkylated with higher carbon number olefins having from about ten to about fifteen carbon atoms per molecule to produce linear alkylbenzenes which are then sulfonated to produce detergents. The feed hydrocarbon may also be reacted with an alkylating agent chosen from a variety of compounds including monohydric alcohols and the previously referred to olefins. Examples of alcohols which may be employed as the alkylating agent include ethanol and methanol. Methanol, for instance, is widely described in the literature as being useful in the para selective methylation of benzene and toluene.

The total quantity of catalyst used in the process is preferably divided into a number of fixed (nonmoving) beds located in individual cylindrical outer vessel(s). While two or more of the catalyst beds could theoretically be located in the same vessel, it is mechanically difficult to segregate in such an arrangement the liquid and vapor flows which may be encountered during regeneration in some embodiments of the invention. The catalyst-retaining vessels are provided with an effective means to feed and withdraw fluid process streams, preferably liquid, between each catalyst bed. In a multi-bed vessel these means will normally comprise two screens, which retain the catalyst particles within their respective beds, plus liquid collection, admixture and distribution devices located between the two screens and employed to provide a uniform flow of the process stream which is passing into or out of the bed across the entire cross-section of the bed. Such devices are employed in the widely utilized simulation of countercurrent liquid-phase adsorptive separation processes. Examples of these devices are provided in U.S. Pat. Nos. 3,208,833; 3,214,247 and 3,523,762 issued to D. B. Broughton and 4,378,292 issued to M. E. Hasse.

The valving used to distribute the reactants to the different zones of the alkylation zone may be in the form of the rotary valves described in U.S. Pat. Nos. 2,985,589; 3,040,777; 3,192,954; 3,422,848; 4,574840; 4,614,205 and 4,633,904. Alternatively, a complex of dual or multiport valves can be used to direct the various process streams including the hydrogen-rich stream as shown in U.S. Pat. Nos. 4,360,362 to S. Asztalos and 4,434,051 to M. W. Golem. Simulated moving bed separation processes are described in the previously cited U.S. Pat. No. 2,985,589 and in U.S. Pat. Nos. 3,291,726; 3,310,486 and 4,498,991 which are incorporated herein for their teaching as to the use of simulated moving beds of solids in process applications. It is to be noted however that the subject process differs from these processes in not using a "pump around" stream such as that carried by line 5 of previously cited U.S. Pat. No. 4,008,291.

It is postulated that a significant portion of the deactivation seen during the use of solid bed alkylation catalysts results from the reaction of the feed olefin(s) to form dimers, trimers or even heavier polymeric entities which clog catalyst pores and/or block active sites on the catalyst. In order to counteract this mode of deactivation, a limited embodiment of the invention employs an alkylation catalyst which has a hydrogenation function which is selective for the hydrogenation of the olefinic dimers located on the catalyst together with hydrogen dissolved in a circulating hydrocarbon to regenerate the catalyst. The use of such a catalyst is however not necessary to the performance of the subject invention.

A highly active metal hydrogenation component on the catalyst will promote hydrogenation of the feed olefin. This potential waste of the olefin and hydrogen can be avoided by careful design and operation of the process to avoid having both the olefin and hydrogen in simultaneous contact with the catalyst. This can be done by flushing one of these materials from a catalyst bed before inserting a stream containing the other compound as described below.

The overall process flow of the subject invention can be best described by reference to the Drawing. FIG. 1 is a simplified flow diagram of the motor fuel alkylation embodiment of the invention. The drawing shows only the reaction and regeneration zones of the overall process since the valving, feed supply and product recovery facilities may be of conventional design. A first feed stream comprising an admixture of isobutane and butene(s) from line 1 is passed into the first of a series of five catalyst beds A–E used in this particular embodiment of the invention. All five catalyst beds are considered as located within the alkylation zone as that term is used herein. In the point in time depicted in the drawing catalyst bed E is the first bed in the reaction zone and beds A and B form the regeneration zone. Bed A is being subjected to a long term or severe hydrogen stripping operation for catalyst regeneration. Bed B is being subjected to the mild (liquid-phase wash) regeneration as described herein.

A feed stream comprising a mixture of isobutane and normal butenes enters the reaction zone via line 1. The solid catalyst present within bed E promotes the alkylation reactions which produce at least one $C_8$ branched chain hydrocarbon, which is carried out of the catalyst bed E via line 2 in admixture with the excess isobutane which enters this bed and any unreacted normal butenes. A second feed stream comprising additional butenes is supplied to the reaction zone via line 3 and the butene enriched admixture is then passed into catalyst bed D via line 4. The catalyst present in bed D then promotes the alkylation of additional isobutane with the entering butenes and the production of more $C_8$ branched chain product hydrocarbons. This results in the formation of a second product-containing reaction zone effluent stream removed in line 5. The effluent of catalyst bed D is passed into catalyst bed C via line 7 together with more normal butenes from line 6. The effluent stream of bed C is then discharged via line 8 into a product recovery zone not shown.

This depiction of the process is in accordance with the present perception that interstage olefin injection is the most beneficial mode of operation. This has not yet been verified. All of the olefin could therefore be passed into the reaction zone in the single feed stream of line 1.

The locations of the points at which the various process streams enter and leave the alkylation zone are periodically advanced by one catalyst bed to simulate the cocurrent movement of the catalyst and the liquid flowing through the catalyst beds. A shift of the inlet positions in the opposite direction of fluid flow simulates cocurrent movement of the solids and liquid. A shift in the position of the inlet positions in the direction of fluid flow simulates movement of the solids in the opposite direction (countercurrent flow). The required frequency of these movements is determined by the size of the beds, the stability of the catalyst under the specific conditions being employed in the reaction zone, the time required for regeneration, the desired operating capacity and engineering optimization. The movement should fall within a time period range of 2 minutes to about 24 hours, with longer time periods being preferred. If the catalyst activity or the amount of catalyst permits, a movement period of in excess of 3–5 days would be desirable.

While no buffer zone is shown for this embodiment it is still not desirable to admix fluids containing the olefin and hydrogen. For this reason it is desired to flush hydrogen or the olefin from any bed at the start of any step which would result in the other compound entering this zone. This may be accomplished using liquid isobutane from a line not shown.

Figure 2:
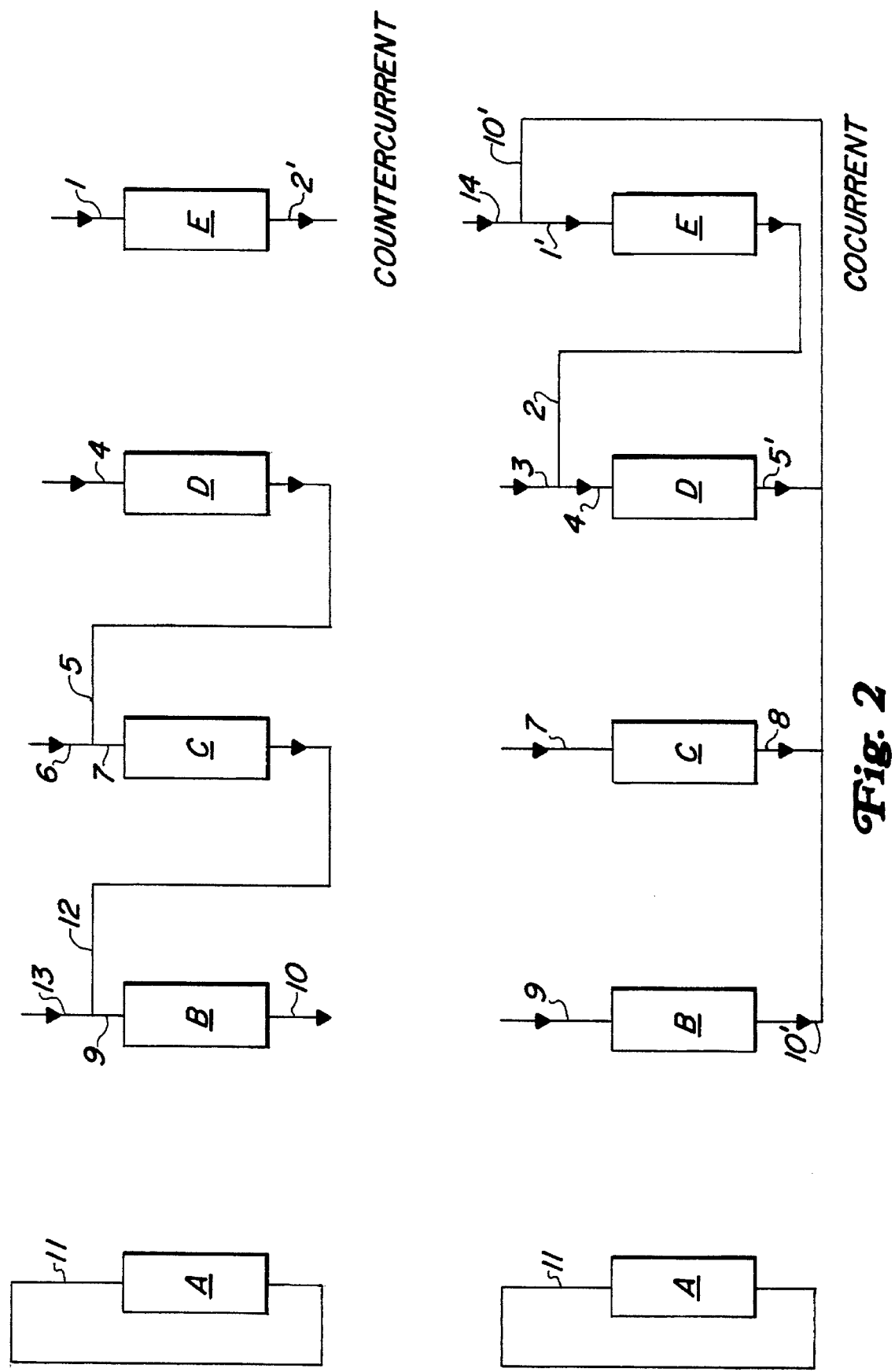
FIG. 2 illustrates the flows in the process unit of FIG. 1 when the process flows are indexed one step in a simulation of the countercurrent flow of catalyst and reactants (top) and the cocurrent flow of catalyst and reactants (bottom).

FIG. 2 illustrates what would happen at one such periodic movement of the points of process stream transfer. The top drawing simulates countercurrent flow. Therefore at the beginning of the next step in the simulation, the isobutane-containing first feed stream would enter catalyst bed D, the butene-containing second stream would enter catalyst bed C and the effluent of bed B would be removed for recovery of the product hydrocarbon. Beds B, C, and D would form the reaction zone. Beds A and E would form the regeneration zone. At the end of each step the stream feed points are moved one bed so the reaction zone moves through beds B, C, D and E. The sequence is then continuously repeated. The rotation of bed A in the regeneration zone is explained below.

The bottom drawing in FIG. 2 depicts the zones of FIG. 1 after one step or increment in the movement of the inlets and outlets in a manner which simulates the cocurrent flow used in the subject invention. The stream specific inlet positions moved to the right in the direction opposite to fluid flow, which simulates movement of the catalyst bed to the left (in the direction of fluid flow). The first bed stream comprising isobutane and butenes now enters bed B via line 9. The effluent of bed B is passed via lines 10' and 11' into catalyst bed E. The secondary olefin feed streams are fed into beds E and D respectively by lines 3 and 14. Bed A remains on the more severe long term hydrogen regeneration and bed C starts the less severe liquid-phase catalyst regeneration step. The effluent of bed D is charged to the product recovery facility via line 5'.

While the drawing shows five catalyst beds being used in the process, there is no requirement to use this number of beds or any specific number of beds. The process can be performed with a much larger number of beds such as the 24–30 beds which are often employed in the simulated movement of adsorbent in the adsorptive separation processes referred to above. There is also no requirement that the individual catalyst beds are located in separate vessels. All of the beds can be located in one or more large vessels similar to those often used in simulated moving bed adsorptive separation processes. However, due to the need to segregate vapor and liquid flows, it is preferred to have only one or two beds in any one vessel. The relative amounts of catalyst located in the reaction zone and regeneration zones can vary from that implied by the drawing although it is preferred that at any one time at least 25 volume percent of the total catalyst located in the overall alkylation zone is employed in the reaction zone and an different 25 percent of the total catalyst is located in the regeneration zone. The regeneration zone may contain as many, or more, beds of catalyst than the reaction zone. The catalyst in each bed is preferably "fixed" rather than fluidized or ebulated. The requirement for the catalyst to be fixed does not require that it cannot be replaced if desired by fresh catalyst on a bed-by-bed basis.

Figure 3:
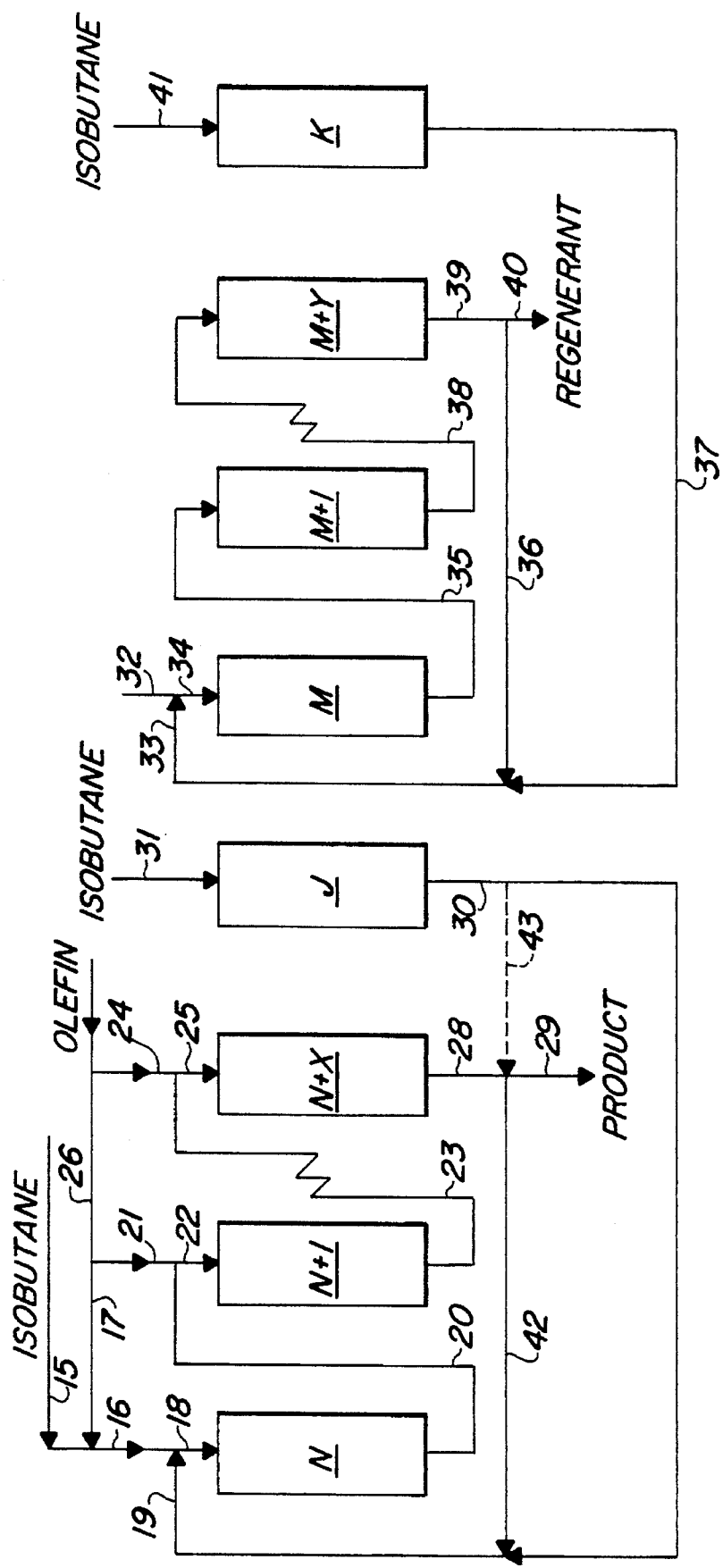
FIG. 3 illustrates a generalized eight bed cocurrent alkylation process employing a number of optional reactant flow variations.

FIG. 3 illustrates an eight bed cocurrent alkylation process in which isobutane in the feed stream of line 15 is reacted with the olefin(s) present in the olefin feed stream of line 27. While more detailed than the other Figures it also does not illustrate the required control systems and temperature control means such as interstage heat exchangers which would be employed on the process. A first portion of the olefin feed stream of line 27 flows into line 16 via lines 26 and 17 and joins with the feed isobutane stream. This admixture flows through line 16 and is optionally admixed with a recycle stream of line 19. This optional recycle stream carries unconsumed isobutane to the first reaction zone thus increasing the paraffin to olefin ratio in the reaction zone. It also increases the mass flow through the individual catalyst beds of the reaction zone, which makes it easier to moderate the temperature rise caused by the alkylation reaction. Unfortunately the recycle stream also comprises the product hydrocarbon which is believed detrimental to catalyst stability.

The contents of lines 16 and 19 flow into the first reactor of the reaction zone, labeled as reactor N, via line 18. The catalyst in reactor N causes the isobutane and substantially all of the added olefin to react forming a desired alkylate hydrocarbon. This product hydrocarbon and the excess isobutane form a first effluent stream which is withdrawn via line 20 and admixed with an additional olefin feed stream from lines 21 and 26. This admixture is passed via line 22 into a second reactor, labeled as reactor N+1, and the added olefin is consumed in the production of a second quantity of the product alkylate. The effluent of this reactor is transferred to the next reactor via line 23. The wider spacing between the reactors and the jog in line 23 are intended to represent the possible numerous reactors which may be employed between reactor N+1 and the final reactor in the reaction zone labeled as reactor N+X. The contents of line 23 is admixed with a third olefin feed stream from line 24 and then passed into reactor N+X via line 25. An additional quantity of alkylate is produced in the reactor and becomes part of the effluent stream of line 28. A first portion of the effluent of this last reactor in the reaction zone is employed as the optional recycle stream charged to the first reactor via line 42 and the remaining second portion is discharged from the process as the product stream of line 29.

Reactor J is at this time being used as a buffer zone to prevent the passage of olefin into the regeneration zone. Isobutane from line 31 flows through reactor J and flushes any residual olefin into reactor N via line 30. Besides recovering the olefin for use in the process this also aids in increasing the paraffin to olefin ratio in the reaction zone. During the initial period of this flush step, the effluent of Bed J can bed directed through optional line 43 to allow the direct recovery of product hydrocarbon trapped in Bed J during the step change in transfer points.

Reactor M is the first reactor in the regeneration zone. An isobutane-rich stream from line 32 is admixed with the recycle stream of line 33 and passed into the reactor M via line 34. Preferably the isobutane of line 32 will contain dissolved hydrogen. The effluent of reactor M, carried by line 35, will be rich in isobutane but will contain a very small concentration of the materials removed from the catalyst in reactor M. The effluent of reactor M is passed via line 35 into the next reactor, reactor M+1. The effluent of reactor M+1 is passed into the next reactor. The jog in line 38 and the different spacing is again intended to indicate that one or more reactors can be located between reactor M+1 and reactor M+Y.

The effluent of the next to last reactor is passed into the last reactor in the regeneration zone via line 38. The effluent of the last reactor in the regeneration zone is withdrawn in line 39 and divided to provide a first portion which is recycled to the beginning of the regeneration zone via lines 36 and 33. The remaining isobutane rich portion is withdrawn from the process via line 40 for recovery of the isobutane in an appropriate separation zone. This separation zone can comprise a fractionation column which removes high boiling hydrocarbons derived from the catalyst which is being regenerated. A second buffer zone is formed by reactor K. A stream of liquid-phase isobutane from line 41 passes through this reactor and flushes out any residual hydrogen. The effluent of the second buffer zone is recycled to the inlet of the regeneration zone via line 37.

FIG. 3 does not show a separate reactor undergoing vapor phase regeneration. Such regeneration is believed desirable, but is not required to employ the subject process.

The steps of the subject process preferably include the regeneration of catalyst located in at least one catalyst bed by contact with a liquid-phase hydrocarbon, which is preferably the feed hydrocarbon such as isobutane. Hydrogen is preferably dissolved in this liquid-phase stream up to the point of the stream being saturated with hydrogen. The catalyst bed which is subjected to regeneration in the next step in the process is preferably the "last" catalyst bed in the reaction zone. This is the catalyst bed in the reaction zone which is furthest removed from the point at which the mixed feed of isoparaffin and olefin enters the process. It can also be described as the catalyst bed from which the alkylation product is removed for passage into the product recovery zone. Therefore when the feed point locations are indexed this last catalyst bed enters the regeneration zone.

The liquid-phase hydrocarbon regeneration step is preferably performed for about 2 minutes to 24 hours at a temperature of from about 30 to about 130 degrees C. Further information on the regeneration of the subject catalyst may be obtained from U.S. patent application Ser. No. 08/043,954, now U.S. Pat. No. 5,310,713.

The steps of the subject process preferably, but not necessarily, include a second regeneration step in which the catalyst is contacted with a vapor-phase gas stream at an elevated temperature in the range of about 80 to about 500 degrees C. and more preferably from 100° to 200° C. This "hydrogen stripping" or severe regeneration step is performed for a longer period of time than the liquid-phase regeneration step and may be performed for about 12 to 48 hours. This regeneration step is preferably performed on a catalyst bed which has just been subjected to the shorter liquid-phase regeneration step. It is a vapor-phase operation performed using a hydrogen rich gas stream but the presence of some isobutane may be desirable to increase the heat capacity of the gas and heat up rates. The longer time required for this regeneration step means that it is not possible to simply increment the positions of the inlets and outlets in a cyclic pattern through all of the catalyst beds. Instead, the valving mechanism must provide for isolating this bed from the system and allowing it to remain in the hydrogen-regeneration mode while the other catalyst beds cycle through one or more steps of the process.

It is a characteristic of the process that the different liquid-phase process streams preferably flow through each of the catalyst beds in the same direction. One exception is any bed which is isolated from the process for high severity regeneration, which may have flows in either direction.

It will be appreciated by those skilled in the art that it is normally unadvisable to pass a hydrogen-containing regenerant stream into a catalyst bed containing olefins or to pass olefins into a catalyst bed containing available hydrogen. Either situation results in a loss of valuable olefins. This is especially true when the catalyst has a hydrogenation metal component. It is therefore preferred to isolate the reaction and regeneration zones in a manner which prevents this intermixture. This can be done using a buffer zone at each end of the reaction zone by any other suitable means. Such buffer zones are flushed by a hydrocarbon stream free of hydrogen and olefin prior to the passage of a process stream containing the other hydrogenation reactant into the buffer zone. The feed hydrocarbon, e.g., isobutane, will normally be a suitable for flushing olefins from a catalyst bed prior to liquid-phase regeneration.

One embodiment of the subject invention can accordingly be characterized as a simulated moving bed process for the alkylation of a feed hydrocarbon which comprises the steps of passing a first feed stream, which comprises a feed hydrocarbon, and an alkylating agent into a first catalyst bed of a multibed reaction zone with the first catalyst bed containing a fixed bed of a solid alkylation catalyst and operated at alkylation-promoting conditions, reacting the feed hydrocarbon and the alkylating agent to produce a product hydrocarbon while the feed stream passes through the reaction zone and thereby forming a first catalyst bed effluent stream comprising the feed hydrocarbon and the product hydrocarbon; passing a second feed stream, which comprises the alkylating agent, and the first catalyst bed effluent stream into a second catalyst bed comprising a fixed bed of the solid alkylation catalyst and operated at alkylation promoting conditions, reacting the feed hydrocarbon and the alklating agent to produce an additional quantity of the product hydrocarbon and thereby forming a second catalyst bed effluent stream comprising the feed hydrocarbon and the product hydrocarbon; passing a third feed stream, which comprises the alkylating agent, and the second catalyst bed effluent stream into a third catalyst bed comprising a fixed bed of the solid alkylation catalyst and operated at alkylation promoting conditions, reacting the feed hydrocarbon and the alklating agent to produce an additional quantity of the product hydrocarbon and thereby forming a third catalyst bed effluent stream comprising the feed hydrocarbon and the product hydrocarbon; from withdrawing the third catalyst bed effluent stream from the process and recovering the product hydrocarbon; passing a liquid-phase regenerant stream through a fourth catalyst bed comprising at least one fixed bed of the solid alkylation catalyst and operated at regeneration conditions; and, periodically advancing the locations at which the first, second and third feed streams enter the process and the identity of the catalyst bed undergoing regeneration to simulate the cocurrent movement of the beds of catalyst relative to the direction of liquid-phase reactant flow through the reaction zone.

A preferred embodiment of the subject invention can be characterized as a simulated moving bed process for the alkylation of a feed hydrocarbon which comprises the steps of passing a first feed stream, which comprises a feed hydrocarbon, and an alkylating agent into a first catalyst bed of a multi-catalyst bed reaction zone, with the first catalyst bed containing a fixed bed of a solid alkylation catalyst and operated at alkylation-promoting conditions, reacting the feed hydrocarbon and the alkylating agent to produce a product hydrocarbon while the feed stream passes through the reaction zone and thereby forming a first catalyst bed effluent stream comprising the feed hydrocarbon and the product hydrocarbon; passing a second feed stream, which comprises the alkylating agent, and the first catalyst bed effluent stream into a second catalyst bed of the reaction zone, with the second catalyst bed comprising a fixed bed of the solid alkylation catalyst and operated at alkylation promoting conditions, reacting the feed hydrocarbon and the alklating agent to produce an additional quantity of the product hydrocarbon and thereby forming a second catalyst bed effluent stream comprising the feed hydrocarbon and the product hydrocarbon; passing a third feed stream, which comprises the alkylating agent, and the second catalyst bed effluent stream into a third catalyst bed located in said reaction zone and comprising a fixed bed of the solid alkylation catalyst and operated at alkylation promoting conditions, reacting the feed hydrocarbon and the alklating agent to produce an additional quantity of the product hydrocarbon and thereby forming a third catalyst bed effluent stream comprising the feed hydrocarbon and the product hydrocarbon; withdrawing the effluent of the last catalyst bed in the reaction zone from the process and recovering the product hydrocarbon; passing a liquid-phase regenerant stream comprising the feed hydrocarbon and a hereinafter characterized recycle stream into and through a first catalyst bed of a regeneration zone which comprises at least two catalyst beds, with each catalyst bed in the regeneration zone comprising a fixed bed of the solid alkylation catalyst and operated at regeneration conditions; passing a stream comprising the feed hydrocarbon into each of a first and second buffer zones located between the reaction and regeneration zones, with each buffer zone comprising a bed of solid catalyst, and with the effluent of first buffer zone being passed into the inlet of the first reaction zone of the reaction zone and with the effluent of the second buffer zone being passed into the first reaction zone of the regeneration zone; and, periodically advancing the locations at which the first, second and third feed streams enter the reaction zone, the location at which the effluent of the last catalyst bed in the reaction zone is withdrawn and the identity of the catalyst beds undergoing regeneration to simulate the cocurrent movement of the beds of catalyst relative to the direction of liquid-phase reactant flow.

The subject process can be performed using any solid, that is, heterogeneous, catalyst which is stable and has the required activity and selectivity for the desired reaction at the conditions needed to maintain liquid-phase reactants in the reaction zone. A large number of catalysts have been proposed for the production of motor fuel by alkylation including various zeolites and superacid catalysts. For instance, U.S. Pat. No. 4,384,161 describes the use of a large pore zeolite and a Lewis acid. The zeolites referred to include ZSM-4, ZSM-3, the faujasites including zeolite Y and mordenite. The Lewis acids mentioned in this reference include boron trifluoride and aluminum chloride. The alkylation of isoparaffins using a somewhat similar catalyst system comprising a large pore crystalline molecular sieve such as a pillared silicate or an aluminophosphate or silicoaluminophosphate together with a gaseous Lewis acid is disclosed in U.S. Pat. No. 4,935,577. The use of these Lewis acids is not preferred in the subject process as they provide their own waste handling and safety problems. They also will probably require provisions for the circulation of the Lewis acid, which may complicate the process as shown by the teaching of the just cited U.S. Pat. No. 4,935,577. U.S. Pat. No. 5,157,200 describes an isoparaffin alkylation process using a catalyst comprising a crystalline transition alumina, preferably eta or gamma alumina, which has been treated with a Lewis acid under anhydrous conditions. Previously referred to U.S. Pat. No. 5,157,196 describes an isoparaffin alkylation process using a slurried solid catalyst, with the preferred catalyst being an acid washed silica which has been treated with antimony pentafluoride. Both of these last two references describe a number of prior art solid bed paraffin alkylation catalysts.

A preferred paraffin alkylation catalyst comprises a refractory inorganic oxide impregnated with a monovalent cation, especially an alkali metal cation or an alkaline earth metal cation, and whose bound surface hydroxyl groups have been at least partially reacted with a Friedel-Crafts metal halide. Analogs of these catalysts without the metal cations are described in U.S. Pat. Nos. 2,999,074 and 3,318,820 which describe preparation techniques which can be applied to the preferred catalysts. The preferred refractory oxide is alumina having a surface area greater than 50 $m^2/g$, but the use of other oxides including titania, zirconia, silica, boria and aluminum phosphate is contemplated. The preferred catalyst also contains a metal component active for olefin hydrogenation deposited on the inorganic oxide prior to reaction of the bound surface hydroxyl groups with the metal halides. This metal may be chosen from the group consisting of nickel, platinum, palladium, and ruthenium with the first three of these metals being preferred. The catalyst contains one or more monovalent metal or alkaline earth metal cations selected from the group consisting of lithium, sodium, potassium, cesium, silver, copper, beryllium, magnesium, calcium and barium. Subsequent to the deposition of these metals and the controlled calcination of the composite, the composite is reacted with a Friedel-Crafts metal halide. The metal may be aluminum, zirconium, tin, tantalum, gallium, antimony or boron. Suitable halides are the fluorides, chlorides and bromides.

Silicalites have been described as useful alkylation catalysts for the production of monoalkylbenzenes in U.S. Pat. No. 4,489,214 to J. R. Butler et al. and as useful in methylating toluene to produce paraxylene in U.S. Pat. No. 4,444,989 issued to F. E. Herkes. The use of ZSM-5 zeolites in aromatic alkylation is described in U.S. Pat. No. 3,751,506. ZSM-5 zeolites that have been treated with one or more compounds or elements to improve their selectivity for para-selective alkylation of aromatic hydrocarbons are described in U.S. Pat. No. 4,420,418. The use of zeolite L, zeolite Omega and zeolite beta as alkylation catalysts for the selective alkylation of benzene is described in U.S. Pat. No. 4,301,316. The use of a number of natural and synthetic zeolites including clinoptilolite and zeolite Y as alkylation catalysts is described in U.S. Pat. No. 3,251,897.

Suitable operating conditions for the reaction zone include a temperature of about −50 to 100 degrees C., preferably 30 to 80 degrees C., and a pressure as required to maintain the hydrocarbons present as a liquid. A moderate pressure in the general range of 120 to 3500 kPa is preferred. A high paraffin to olefin (reactor entrance) of 10:1 to 50:1 is preferred. The weight hourly space velocity for the olefin may range from about 0.1 to 1.0 $hr^{-1}$.

It is generally preferred that the reaction zone is operated with an excess of the feed hydrocarbon compared to the alkylating agent. That is, it is preferred to operate with a ratio of the feed paraffinic or aromatic hydrocarbon to a feed olefin greater than 1:1, and preferably from about 2:1 to about 5:1 or higher as measured by the flow rates into the reaction zone. It is highly preferred to operate with an abundance of isoparaffin compared to alkylating agent in a motor fuel alkylation process. Specifically, it is preferred that the molar ratio of isoparaffin to olefin being charged to the reaction zone is greater than 2:1 and more preferably greater than 3:1. Ratios from 10:1 to about 100:1 or higher can be employed for motor fuel alkylation. The known technique of feeding the olefin at a number of points along the flow path of the feed hydrocarbon may be employed to maintain a higher average paraffin to olefin ratio.

Provisions may be made for removing catalyst from the reaction zone in order to replace the catalyst with fresh or regenerated catalyst. One such system for this is described in U.S. Pat. No. 4,973,780 to R. C. Johnson et al.

The exothermic nature of the alkylation reaction must be considered in any design. Operation at the preferred high paraffin to olefin ratios will provide a large mass flow through the reaction zone which will provide a heat sink. Heat can be and preferably is removed from the process by indirect heat exchange carried out between the catalyst beds. It is possible to remove heat from the catalyst beds by indirect heat exchange through the use of heat exchangers in contact with the catalyst or process streams within the catalyst beds. Relatively cool feed hydrocarbon or olefin can be injected into the reaction zone to moderate the temperature.

COMPARATIVE EXAMPLE

A small scale pilot plant having eight catalyst beds was used to perform tests on solid alkylation catalysts. Each catalyst bed was loaded with 20 cc of the preferred (potassium modified platinum and aluminum chloride on alumina) solid catalyst described herein. The plant was configured to allocate two beds to the reaction zones, four beds to regeneration by hydrogen-containing liquids and two beds to buffer zones between the reaction and regeneration zone. The reaction zone was operated at a weight hourly space velocity (WHSV) of 0.23 $hr^{-1}$ based upon olefin feed, an external paraffin to olefin ratio of 45:1 into each bed and a temperature of 30 degrees C. A mixture of isobutane and normal butenes was charged to the first bed of the reaction zone. A second feed stream of normal butenes was charged to the second bed of the reaction zone. The step time for incrementing the feed and product points was set at 30 minutes. The regeneration zone was flushed with hydrogen saturated isobutane at 30 degrees C. No high severity (hydrogen stripping) regeneration was performed.

The unit was operated in accordance with the prior art with the countercurrent flow of the catalyst and the process stream through the reaction zone being simulated. It was determined that the catalyst deactivated much faster than expected from the results of traditional once through tests. Catalyst activity compared to the fresh catalyst fell to about 10 percent after 17 hours on stream. While the liquid-phase regeneration was being performed at lower than optimum temperature, the rate of deactivation indicated the occurance of some unexpected deactivation mechanism.

Product quality is believed to be related to catalyst activity. Cocurrent catalyst-reactant flow was therefore tried in an effort to increase product quality. This second test was performed using the same pilot plant and catalyst but with the two bed reaction zone operated to simulate cocurrent movement. The reactants and operating conditions were also the same as the countercurrent test. This test was run for a total of 60 hours with the surprising and unexpected result that little deactivation of the catalyst being noted. The test was terminated because the supply of reactants was exhausted.

The results of this test were so surprising that it was repeated for purposes of verification. The second cocurrent run continued for 275 hours with the catalyst still having 83% of its initial activity after 200 hours on stream.

It is believed that a commercial scale operation which would allow the use of higher temperature liquid-phase regeneration would have increased catalyst stability even more.

A third cocurrent test was performed using the same plant, catalyst and conditions except that the cycle time was reduced to 20 minutes. In this test the catalyst deactivated more rapidly, but it is believed this was due to an impurity in one of the feed streams.

The mechanism responsible for the much faster rate of deactivation during countercurrent operation is not known. However, it has been hypothesized that it is at least partly caused by the internal recycling of the reaction product in the reaction zone which occurs during countercurrent flow. By this it is meant that advancing the feed stream inlet points to the next position results in the liquid material in the interparticle and intraparticle void spaces being moved upstream one bed, combined with more olefin and then passed over the catalyst again.

Countercurrent flow thereby increases the product/olefin ratio at the front of the reactor which is believed to cause the increased deactivation rate. The paraffin product can react with the olefin forming higher molecular weight products which accumulate on the catalyst. For example, if enough olefin is added to each bed to result in a 2 percent product yield, then a straight-through two catalyst bed reaction zone produces a reaction zone having a maximum product concentration of 4 percent. A countercurrent flow system results in the product collecting in the reaction zone such that calculated peak product concentrations on the order of 6–16 percent are experienced.

Another difference is that the regenerated catalyst "moves" to the last catalyst bed position in countercurrent flow operation but to the first catalyst bed in the reaction zone during simulated cocurrent flow.

What is claimed:

1. A simulated cocurrent moving bed process for the alkylation of a feed hydrocarbon performed in an apparatus comprising individual beds of catalyst divided between a multibed alkylation zone and a regeneration zone, which process comprises the steps of:
   (a) passing a first feed stream, which comprises a feed hydrocarbon, and an alkylating agent into a first catalyst bed of the multibed reaction zone with the first catalyst bed containing a fixed bed of a solid alkylation catalyst and operated at alkylation-promoting conditions, reacting the feed hydrocarbon and at least a portion of the alkylating agent to produce a product hydrocarbon while the feed stream passes through the reaction zone and thereby forming a first catalyst bed effluent stream comprising the feed hydrocarbon and the product hydrocarbon;
   (b) passing the first catalyst bed effluent stream into a second catalyst bed of the reaction zone, with the second catalyst bed comprising a fixed bed of the solid alkylation catalyst and being operated at alkylation promoting conditions, reacting the feed hydrocarbon and the alkylating agent to produce an additional quantity of the product hydrocarbon and thereby forming a second catalyst bed effluent stream comprising the feed hydrocarbon and the product hydrocarbon;
   (c) recovering the product hydrocarbon;
   (d) passing a regenerant stream through the regeneration zone, which comprises a third catalyst bed comprising a fixed bed of the solid alkylation catalyst and is operated at regeneration conditions; and,
   (e) periodically advancing the locations at which the first feed stream and the regenerant stream enter the process, and the second catalyst bed effluent stream is removed from the process to simulate the cocurrent movement of the beds of catalyst relative to the direction of liquid-phase reactant flow.

2. The process of claim 1 further comprising the step of passing a second feed stream, which comprises the alkylating agent into the second catalyst bed.

3. The process of claim 2 further comprising the step of passing a third feed stream, which comprises the alkylating agent, and the second catalyst bed effluent stream into a fourth catalyst bed comprising a fixed bed of the solid catalyst and producing an additional quantity of the product hydrocarbon, and recovering the product hydrocarbons from the effluent of the fourth catalyst bed.

4. The process of claim i further characterized in that the regenerant stream comprises a liquid-phase hydrocarbon and dissolved hydrogen.

5. The process of claim 4 further comprising the step of subjecting an additional catalyst bed to a vapor-phase regeneration in which the catalyst bed is contacted with a hydrogen-rich vapor stream.

6. The process of claim 1 further characterized in that the feed hydrocarbon is a paraffin.

7. The process of claim 1 further characterized in that the feed hydrocarbon is an aromatic hydrocarbon.

8. A simulated moving bed process for the alkylation of a feed hydrocarbon comprising the steps of:
   (a) passing a first feed stream, which comprises a feed hydrocarbon, and an alkylating agent into a first catalyst bed of a multibed reaction zone with the first catalyst bed containing a fixed bed of a solid alkylation catalyst and operated at alkylation-promoting conditions, reacting the feed hydrocarbon and the alkylating agent to produce a product hydrocarbon while the feed stream passes through the reaction zone and thereby forming a first catalyst bed effluent stream comprising the feed hydrocarbon and the product hydrocarbon;
   (b) passing a second feed stream, which comprises the alkylating agent, and the first catalyst bed effluent stream into a second catalyst bed comprising a fixed bed of the solid alkylation catalyst and operated at alkylation promoting conditions, reacting the feed hydrocarbon and the alkylating agent to produce an additional quantity of the product hydrocarbon and thereby forming a second catalyst bed effluent stream comprising the feed hydrocarbon and the product hydrocarbon;
   (c) passing a third feed stream, which comprises the alkylating agent, and the second catalyst bed effluent stream into a third catalyst bed comprising a fixed bed of the solid alkylation catalyst and operated at alkylation promoting conditions, reacting the feed hydrocarbon and the alkylating agent to produce an additional quantity of the product hydrocarbon and thereby forming a third catalyst bed effluent stream comprising the feed hydrocarbon and the product hydrocarbon;
   (d) withdrawing the third catalyst bed effluent stream from the process and recovering the product hydrocarbon;
   (e) passing a liquid-phase regenerant stream through a fourth catalyst bed comprising at least one fixed bed of the solid alkylation catalyst and operated at regeneration conditions; and,
   (f) periodically advancing the locations at which the first, second and third feed streams and the regenerant stream enter the process to simulate the cocurrent movement of the beds of catalyst relative to the direction of liquid-phase reactant flow through the reaction zone.

9. The process of claim 8 further characterized in that the feed hydrocarbon is a paraffin.

10. The process of claim 8 further characterized in that the alkylating agent is an olefin.

11. A simulated moving bed process for the alkylation of a feed hydrocarbon comprising the steps of:
   (a) passing a first feed stream, which comprises a feed hydrocarbon, and an alkylating agent into a first catalyst bed of a multi-catalyst bed reaction zone, with the first catalyst bed containing a fixed bed of a solid alkylation catalyst and operated at alkylation-promoting conditions, reacting the feed hydrocarbon and the alkylating agent to produce a product hydrocarbon while the feed stream passes through the reaction zone and thereby forming a first catalyst bed effluent stream comprising the feed hydrocarbon and the product hydrocarbon;
   (b) passing a second feed stream, which comprises the alkylating agent, and the first catalyst bed effluent stream into a second catalyst bed of the reaction zone, with the second catalyst bed comprising a fixed bed of the solid alkylation catalyst and operated at alkylation promoting conditions, reacting the feed hydrocarbon and the alkylating agent to produce an additional quantity of the product hydrocarbon and thereby forming a second catalyst bed effluent stream comprising the feed hydrocarbon and the product hydrocarbon;

(c) passing a third feed stream, which comprises the alkylating agent, and the second catalyst bed effluent stream into a third catalyst bed located in said reaction zone and comprising a fixed bed of the solid alkylation catalyst and operated at alkylation promoting conditions, reacting the feed hydrocarbon and the alkylating agent to produce an additional quantity of the product hydrocarbon and thereby forming a third catalyst bed effluent stream comprising the feed hydrocarbon and the product hydrocarbon;

(d) withdrawing the effluent of the last catalyst bed in the reaction zone from the process and recovering the product hydrocarbon;

(e) passing a liquid-phase regenerant stream comprising the feed hydrocarbon and a hereinafter characterized recycle stream into and through a first catalyst bed of a regeneration zone which comprises at least two catalyst beds, with each catalyst bed in the regeneration zone comprising a fixed bed of the solid alkylation catalyst and operated at regeneration conditions;

(f) passing a stream comprising the feed hydrocarbon into each of a first and second buffer zones located between the reaction and regeneration zones, with each buffer zone comprising a bed of the solid alkylation catalyst, and with the effluent of first buffer zone being passed into the inlet of the first reaction zone of the reaction zone and with the effluent of the second buffer zone being passed into the first reaction zone of the regeneration zone; and, (g) periodically advancing the locations at which the first, second and third feed streams enter the reaction zone, the location at which the effluent of the last catalyst bed in the reaction zone is withdrawn and the location at which the regenerant stream enters the process to simulate the cocurrent movement of the beds of catalyst relative to the direction of liquid-phase reactant flow.

12. The process of claim 11 further characterized in that the feed hydrocarbon is a paraffin and the alkylating agent is an olefin.

13. The process of claim 12 further characterized in that the feed hydrocarbon is isobutane and the alkylating agent is a normal butene.

14. The process of claim 11 further characterized in that a portion of the effluent of the last catalyst bed in the regeneration zone is recycled to the inlet of the first catalyst bed in the regeneration zone.

15. The process of claim 11 further characterized in that the regeneration zone comprises at least as many catalyst beds as the reaction zone.

* * * * *